US00PP13793P39

(12) United States Plant Patent
Pieters

(10) Patent No.: US PP13,793 P3
(45) Date of Patent: May 13, 2003

(54) CHRYSANTHEMUM PLANT NAMED 'GEDI ONE OATL'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,922

(22) Filed: Jun. 4, 2001

(65) Prior Publication Data

US 2003/0028940 P1 Feb. 6, 2003

(51) Int. Cl.[7] ..... A01H 5/00
(52) U.S. Cl. ..... Plt./295

(58) Field of Search ..... Plt./295, 286, 296

(56) References Cited

U.S. PATENT DOCUMENTS

PP10,181 P 1/1998 Wain ..... Plt./296

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a daisy type inflorescence, consistent flowering response to short days, blooming consistently after 49 days of short day length, free branching habit, highly flexible plant habit, and very uniform round growth habit.

1 Drawing Sheet

LATIN NAME

*Dendranthema morifolium.*

VARIETY

Figure 1:
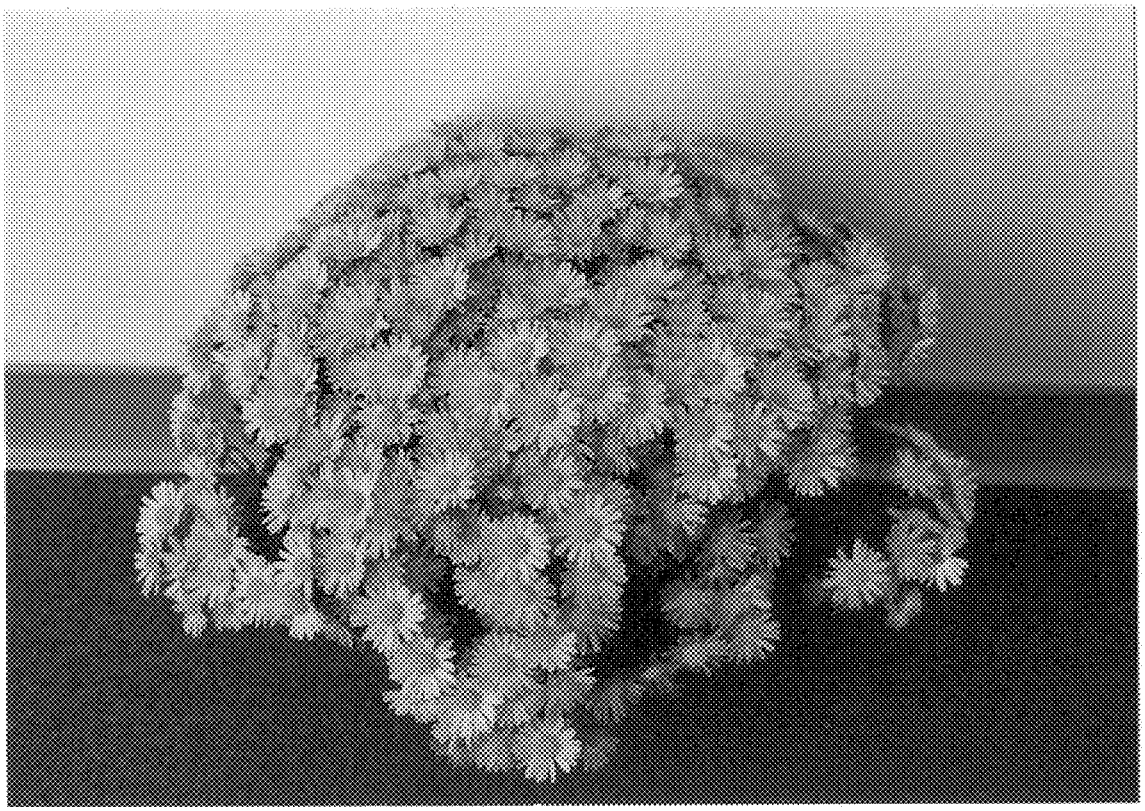

'GEDI ONE OATL'.

BACKGROUND OF THE INVENTION

The present invention relates to a new and distinct cultivar of Chrysanthemum plant, botanically known as *Dendranthema morifolium* and herein after referred to by the cultivar name 'GEDI ONE OATL'.

This new cultivar originated from a naturally occurring mutation on a single branch of the Chrysanthemum cultivar 'Atlantico' (unpatented in the United States). The new cultivar was discovered by the inventor in October 1998.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'GEDI ONE OATL' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GEDI ONE OATL'. These observations were made on plants approximately 125 days old from rooted cuttings. These characteristics in combination distinguish 'GEDI ONE OATL' as a new and distinct Chrysanthemum:

1. Daisy type inflorescence;

2. Consistent flowering response to short days, blooming consistently after 49 days of short day length;

3. Free branching habit;

4. Highly flexible plant habit; and

5. Very uniform round growth habit.

Plants of the new cultivar are similar to plants of the 'Atlantico' parent cultivar in most horticultural characteristics, however plants of the new cultivar differed from plants of the 'Atlantico' cultivar in ray floret color.

The new cultivar can be compared to the Chrysanthemum cultivar 'Oriole' (disclosed in U.S. Plant Pat. No. 10,181). However plants of the new Chrysanthemum differed from the plants of the cultivar 'Oriole' in the following characteristics:

1. The new cultivar naturally blooms approximately 2 weeks earlier;

2. The new cultivar has a more round plant shape and greater branching; and

3. The new cultivar has more blooms per flowering branch.

BRIEF DESCRIPTION OF THE PHOTOGRAPHS

The photograph shows a plant of 'GEDI ONE OATL' grown in a 1-gallon container. A single cutting was grown in the container and planted at the end of June. The plants were grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000. The growing conditions range from 60° to 65° F. at night to 70° to 85° F. during the day. Measurements and numerical values represent averages of typical flowering types.

Botanical classification: *Dendranthema morifolium* cultivar 'GEDI ONE OATL'.
Commercial classification: Garden-type Chrysanthemum.
Parentage: Naturally occurring mutation on a single branch of the Chrysanthemum cultivar 'Atlantico' (unpatented in the United States).

PROPAGATION

Time to rooting: 7 to 14 days at approximately 21° C.
Root description: Fine, fibrous.

PLANT

Growth habit: Mounding herbaceous perennial.
Height: Approximately 24.5 cm.
Plant spread: Approximately 28 cm.
Growth rate: Moderate.
Branching characteristics: Free Branching.
Internode length: Approximately 2.1 cm.
Length of lateral branches: Approximately 21 cm.
Number of leaves per lateral branch: Approximately 19.

FOLIAGE

Leaf:
*Arrangement.*—Alternate, single.
*Average length.*—Approximately 2.6 cm.
*Average width.*—Approximately 1.9 cm.
*Shape of blade.*—Ovate.
*Apex.*—Acuminate.
*Base.*—Attenuate.
*Attachment.*—Stalked.
*Margin.*—Pinnately lobed and toothed.
*Texture of top surface.*—Lightly pubescent.
*Texture of bottom surface.*—Lightly pubescent.
*Color.*—Young foliage upper side: Near 147A. Young foliage under side: Near 147B. Mature foliage upper side: Near 147A. Mature foliage under side: Near 147B. Venation upper side: Near 147B. Venation under side: Near 147B.
Petiole:
*Average length.*—Approximately 1.5 cm.
*Color.*—Near 138B.
*Diameter.*—Approximately 0.2 cm.

BLOOM

Inflorescence:
*Flowering habit.*—Induced by darkness period greater than 13.5 hours, approximately 49 days of appropriate day length required to induce and develop blooms.
*Inflorescene form.*—Daisy.
*Natural flowering season.*—Aproximately the last week of August, first week of September.
*Number of inflorescences per stem.*—Approximately 13 to 15.
*Inflorescence diameter.*—Approximately 3.4 cm.
*Inflorescence depth.*—Approximately 0.9 cm.
*Inflorescence longevity on plant.*—Approximately 26–29 days.
*Persistence.*—Persistent.
Ray florets:
*Appearance.*—Matte.
*Texture.*—Smooth.
*Average number per flower.*—Approximately 25 to 30.
*Shape.*—Cylindric.
*Margin.*—Entire.
*Apex.*—Obtuse.
*Length.*—Approximately 1.4 cm.
*Width.*—Approximately 0.4 cm.
*Color.*—Upper surface at first opening: Near 178B. Upper surface at maturity: on 40% nearest to base: Near 7B. Upper surface at maturity: on 60% nearest to apex: Near 166B. Upper surface at fading: on 20% nearest to base: Near 7B. Upper surface at fading: on 80% nearest to apex: Near 166B. Under surface at first opening: Near 178B. Under surface at maturity: on 40% nearest to base: Near 7B. Under surface at maturity: on 60% nearest to apex: Near 166B. Under surface at fading: on 20% nearest to base: Near 7B. Under surface at fading: on 80% nearest to apex: Near 166B. Entire surface of faded ray floret: Near 21D.
Disc florets:
*Appearance.*—Shiny.
*Texture.*—Smooth.
*Average number per flower.*—Approximately 90 to 100.
*Shape.*—Cylindric.
*Apex.*—Obtuse.
*Average length.*—Approximately 0.3 cm.
*Average width.*—Approximately 0.1 cm.
*Average diameter.*—Approximately 0.2 cm.
*Color.*—At first opening: Near 15A. At maturity: Near 15A. At fading: Near 15A.
Peduncle:
*Length.*—At terminal end (shortest): Approximately 5 cm. At lateral end (longest): Approximately 6.7 cm.
*Diameter.*—Approximately.0.2 cm.
*Strength.*—Moderate.
*Color.*—Near 146A.
*Habit.*—Erect.
*Surface texture.*—Pubescent.
Inflorescence bud:
*Length.*—Approximately 0.4 cm.
*Diameter.*—Approximately 0.4 cm.
*Form.*—Globular.
*Color.*—Near 146A.
Phyllaries:
*Appearance.*—Matte.
*Texture.*—Lightly pubescent.
*Number.*—Approximately 15 to 20.
*Shape.*—Ovate.
*Margin.*—Entire.
*Apex.*—Acute.
*Diameter.*—Approximately 0.2 cm.
*Length.*—Approximately 0.3 cm.
*Color.*—Uppper side: Near 137B. Under side: Near 137B.

REPRODUCTIVE ORGANS

Ray florets:
*Number of pistils per flower.*—1.
*Stigma shape.*—2 branched.
*Stigma color.*—Near 15A.
*Stigma length.*—Approximately 0.1 cm.
*Style color.*—Near 144B.
*Style length.*—Aproximately 0.3 cm.
*Stamens.*—Absent.
Disc florets:
*Number of pistils per flower.*—1.
*Stigma shape.*—Cylindric.
*Style length.*—1.0 cm.
*Number of stamens per flower.*—Approximately 5.
*Anther shape.*—Tubular.

*Anther color.*—Near 15A.
*Pollen color.*—Near 15A.

OTHER CHARACTERISTICS

Seed production: Commercially, this plant is not used or observed in a stage wherein seeds would be produced. Therefore, seed production has not been observed.

Flower fragrance: Absent.

Disease resistance: Neither resistance nor susceptibility to diseases and pests have been observed in this cultivar.

What is claimed is:

1. A new and distinct variety of Chrysanthemum plant named 'GEDI ONE OATL' as herein illustrated and described.

* * * * *